US006355456B1

(12) United States Patent
Hallberg et al.

(10) Patent No.: US 6,355,456 B1
(45) Date of Patent: Mar. 12, 2002

(54) PROCESS OF USING WET GRAIN RESIDUE FROM ETHANOL PRODUCTION TO FEED LIVESTOCK FOR METHANE PRODUCTION

(75) Inventors: David E. Hallberg; Victor W. Schlesinger, both of Omaha, NE (US)

(73) Assignee: Dakota Ag Energy, Inc., Sioux Falls, SD (US)

( * ) Notice: Subject to any disclaimer, the term of this patent is extended or adjusted under 35 U.S.C. 154(b) by 0 days.

(21) Appl. No.: 09/487,604

(22) Filed: Jan. 19, 2000

(51) Int. Cl.$^7$ ............................. C12P 7/06; C12P 5/00; A23K 1/08; A23K 1/18
(52) U.S. Cl. ..................... 435/161; 435/166; 426/624; 426/807
(58) Field of Search ................. 435/161, 166; 426/624, 807

(56) References Cited

U.S. PATENT DOCUMENTS

| | | | |
|---|---|---|---|
| 72,827 A | 12/1867 | Embree | 426/624 |
| 87,397 A | 3/1869 | Christie et al. | 426/624 |
| 2,158,043 A | 5/1939 | Grelck | 426/624 |
| 4,018,188 A | 4/1977 | Burdette | 119/28 |
| 4,356,269 A | 10/1982 | Thomsen et al. | 435/316 |
| 4,400,195 A | 8/1983 | Rijkens | 71/10 |
| 4,503,154 A | 3/1985 | Paton | 435/167 |
| 5,047,332 A | 9/1991 | Chahal | 435/32 |

OTHER PUBLICATIONS

Evalulation of Corn and Sorghum Distillers Byproducts, Lodge et al, pp. 37–43, 1997.
1999 Nebraska Beef Report, p. 32, Fanning et al.
Proceedings of the American Society of Animal Science, 1999, Stock et al, 1–12.
Evaluation of Wet Distillers Composite for Finishing Ruminants, Lodge et al, pp. 44–50, 1997.
Feeding Value of Wet Distillers Byproducts for Finishing Ruminants, Larson et al, pp. 2228–2236, 1993.
Uses of Corn Coproducts in Beef and Dairy Rations, Klopfenstein et al, 2001.
Evaluation of Wet Distillers Grains in Finishing Diets for Yearling Steers, A.S. Leaflet R1450, 1997.
Substituting Wet Distillers Grains or Condensed Distillers Solubles for Corn Grain in Finishing Diets for Yearling Heifers, A.S. Leaflet R1451, 1997.
Evaluation of Wet and Dry Distillers Grains and Wet and Dry Corn Gluten Feeds for Ruminants, Firkins et al, Journal of Animal Science, vol. 60, No. 3, 1985.
Wet Corn Distillers Byproducts Compared with Dried Corn Distillers Grains with Solubles as a Source of Protein and Energy for Ruminants, HAM et al, pp. 3246–3257, 1994.

*Primary Examiner*—David M. Naff
*Assistant Examiner*—Mike Meller
(74) *Attorney, Agent, or Firm*—Lorusso & Loud (57) ABSTRACT

An integrated continuous process for the production of ethanol and a bio-gas containing methane is disclosed. The process comprises the following steps. First, grain is fermented in an aqueous medium to produce ethanol in the medium which contains a wet distillers' grain with solubles as a wet grain residue and carbon dioxide. Next, the wet grain is feed to livestock in a feedlot which has slatted floors. The wet grain residue constitutes 25–80% of a feed ration of the livestock on a dry weight basis. The feed ration consists essentially of the 25–80% wet grain residue and grain. Third, the manure from the livestock is collected from beneath the slatted floor. Fourth, the collected manure is digested anaerobically with microorganisms to produce the bio-gas containing methane and, as a residue, a bio-fertilizer. Fifth, the bio-gas is combusted to produce heat. Sixth, the grain is dry milled utilizing heat produced by the combustion.

2 Claims, 3 Drawing Sheets

PROCESS OF USING WET GRAIN RESIDUE FROM ETHANOL PRODUCTION TO FEED LIVESTOCK FOR METHANE PRODUCTION

BACKGROUND OF THE INVENTION

1. Field of the Invention

The present invention relates to a novel integrated process for the environmentally benign use of grains and renewable materials to produce "clean beef" (or milk), fuel ethanol for motor fuel purposes, and bio-gas/bio-fertilizer from animal wastes.

2. Background of the Prior Art

American agriculture in general, and the livestock feeding industry in particular, face increasing pressures which pose challenges to traditional methods of doing business, and offer opportunities to those with improved methods. Trends in the marketplace have created a demand for "clean beef" (beef which is hormone-, antibiotics-, and *E.coli*- free). Environmental authorities at both the national and local levels are imposing requirements on large animal feeding operations to ensure that odor and environmental contamination are substantially reduced from current levels. Cost effective methods of converting animal wastes into marketable fuels and products are needed. These methods and products should be generally "sustainable" (e.g., renewable) and environmentally friendly.

In conventional practice, cattle are normally fed 22 pounds of dry matter equivalent per day with as much as a 50% moisture content for a total feed weight of approximately 44 pounds per day. The moisture content represents a portion of the animal's total daily water intake. Cattle on average convert 6.5 pounds of feed into one pound of body weight gain. If the animal gains 3.5 pounds of weight per day and requires 6.5 pounds of feed per pound of gain, it must consume 22.75 pounds of dry matter feed per day. This diet not only allows for weight gain but provides the energy to sustain the animal in good health. Approximately 70% of the animal's dry matter feed ration is digestible. The non-digestible and water portions are passed as manure and urine which in conventional practice are typically dumped onto the ground. The pens are then occasionally cleaned by scraping the manure and dirt mixture into wind row piles where it sun-dries. The mixture is eventually field applied, sold as fertilizer or disposed of in some fashion. Due to growing environmental concerns, however, manure management is rapidly becoming one of the most critical functions in commercial feeding operations.

Modern feedyards are designed to catch the water runoff from cattle pens in special drain basins or pits which are often aerated to introduce more oxygen into them. The water will evaporate as new runoff continuously refills the pits. They are designed to normally handle up to a 25-year rain runoff However, in just the last 25 years, there have been not only 25-year rains but a 50, 100 and even a 300-year rain in the Midwest. These heavy rains can, and do, overwhelm the feedyards' ability to manage the pen drainage systems.

Since the early 1990's, many states and the federal government have begun to review the public policies regulating commercial cattle feeding. Many complaints have been received from environmentalists, naturalists, fishermen and neighbors regarding the untreated contamination resulting from the feedyards. The sheer volume of cattle waste (12 times that of one adult human per day) is cause for considerable concern. Whereas human waste is treated in sewage disposal plants, septic tanks or by other approved methods, conventionally, cattle waste is not so treated.

The United States has a population of approximately 275 million people and raises approximately 100 million cattle, of which over 32 million are brought together in confined commercial feedlots. If each adult animal produces 12 times as much waste as an adult human being, the United States is producing the animal waste-equivalent of a nation of 385 million people, just in feedyards.

It is these feedyard cattle that are posing the greatest threat to the environment. Cattle on farms and ranches average approximately one animal for each 12 acres or about one animal per 500,000 square feet, whereas, in a confined feedyard operation, one animal has an average of 250 square feet. This animal density concentrates the manure into very small areas and local ecosystems are thereby jeopardized.

Commercial cattle feeding (feedyards larger than 1,000 animal units) are the point source for numerous real and perceived environmental problems: water contamination, airborne particulates, objectionable odors, fly and insect infestations, nitrogen and phosphorus buildup in the soil and major fish kills in rivers and streams. The troublesome greenhouse gas (GHG) emissions of methane is another major environmental problem. Worldwide, cattle are the single largest animal source of methane release into the environment (methane is 22 times more potent than $CO_2$ as a greenhouse gas).

Most states require freshly applied raw animal manure to be incorporated into the soil at a depth of at least nine inches, and within 12 hours of manure application. This is the most economic use of feedyard manure today. Feedyards that recover manure but do not keep it separated and free from dirt contamination, will normally sell the pen scrapings in a dry form. However, this method is more labor intensive and requires additional equipment and real estate for wind row drying. At this point, the waste byproduct can pollute the surrounding environment if washed away during wet periods and the opportunity for odor and insect problems increases.

Another major environmental concern caused by commercial cattle feeding is the build-up of nitrogen and phosphorus in the soil under and around feedyards where manure is applied or disposed of. This build-up comes from the long-term consumption, and then concentration, of feed grain in the relatively small area encompassed by a feedlot. A typical feedyard will consume approximately 20 pounds of corn per animal per day. In a 25,000 head feedyard that is full with year-round operation, this amounts to approximately 3,250,000 bushels of corn per year.

In the corn belt of the upper Midwest each acre of corn receives approximately 135 pounds of nitrogen per acre and will yield approximately 130 bushels of corn per acre. When the mature corn is harvested only the seed is saved and the plant is reincorporated into the soil for nutritional enrichment. The 130 bushels of seed corn taken from the acre contain most of the nitrogen and phosphorus which is then transported to the cattle feedyard for feed rations. If a typical 25,000 head location utilizes 3.25 million bushels per year and the average production is 130 bushels per acre, the feedyard will require all of the output from 25,000 acres of corn.

If a conventional 25,000 head feedyard is built on approximately 250 acres of land, this means the nitrogen and phosphorus is taken from 25,000 acres of corn and ends up on 250 acres of feedlot—a concentration of 100-fold. During the feeding cycle, cattle use approximately one-half of the nitrogen in the corn for body growth by converting it to protein. Thus, this portion of the nitrogen leaves the feedyard as meat. The remaining 50% of nitrogen and 100% of the phosphorus is left behind. The manure management of the feedyard must then move these compounds back to local farm fields as replacement fertilizer needed for next year's corn crop.

If the feedyard does not collect and remove these compounds from the land it will end up in the environment. The nitrogen and phosphorous can remain in the land under the feedyard and be trapped there until the end of the feedyard's life cycle. Or, they can be transported off site via water runoff, airborne particulates, manure removal or disposal, etc. The principal environmental concern is that heavy buildup of nitrogen and phosphorus can enter the water system, as in the widely reported instances of runoff from Midwestern states like Iowa and Illinois into the Mississippi River, and ultimate deposit in heavy concentrations in the Gulf of Mexico and elsewhere, causing immense "dead zones" which cause the death of shrimp and other fish due to oxygen depletion.

While anaerobic digestion of manure has been known for some time, it has never been practiced on a large scale basis in cattle feedlots due to poor economics, inability to prevent manure contamination by soil and water and limited outlets for the bio-methane.

It is clear that a new approach to cattle feeding is needed in order to address the concerns of environmental regulators, consumers, and the economic pressures facing the industry itself.

Recent outbreaks of *E. Coli*-contaminated meat, and growing consumer demand for "clean" beef have combined to put significant pressure on livestock producers, feedlot operators, and meat packers. In the U.S. conventional feeding methods rely upon heavy use of anabolic steroids, antibiotics, and other artificial practices to promote animal weight gain. However, the U.S. Food and Drug Administration (FDA) has expressed growing concern over the threat posed by excessive antibiotics use in animal feeding, which experts now link to the proliferation of drug-resistant bacteria, and increasing humans' vulnerability to untreatable infections.

Moreover, food safety officials have expressed growing concern about the long-term health effects of eating beef which contains high levels of antibiotics and growth hormones, and many nations prohibit the importation of U.S. beef that contains growth-enhancing steroids, hormones, and other "artificial" additives. Consequently, consumer demand for beef has declined.

A recent Presidential Executive Order set a national goal of tripling the production and use of biofuels by the year 2010, in large part due to the need to achieve substantial reductions in emissions of greenhouse gases such as carbon dioxide ($CO_2$) and methane. Primary sources of $CO_2$ are fossil fuel combustion, and a primary source of methane emissions is cattle flatulence and manure. Renewable biofuels such as ethanol and bio-gas using conventional methods are not cost competitive with fossil fuels, and new approaches are needed if the production goals are to be met. One of the most capital- and energy-intensive sections of modern-day ethanol plants is the spent mash (protein co-product) drying and handling section. The protein co-product is valued as an effective feed ingredient for ruminant animals (cattle and dairy cows), but in traditional practice must be dried before it can be transported and stored. Eliminating this requirement would result in substantial capital, energy and operating cost savings in ethanol production.

SUMMARY OF THE INVENTION

Accordingly, one objective of the present invention is to provide an integrated system which makes anaerobic digestion of livestock manure an economically viable operation.

Another object of the present invention is to provide a subsystem for a livestock feedlot which is integrated with ethanol production in such a manner that the economics of both the ethanol production and the feedlot operation are enhanced.

Still another object of the present invention is integration of anaerobic digestion of livestock waste with ethanol production in such a manner that the economics of both the ethanol production and the anaerobic digestion are enhanced.

Yet another object of the present invention is to provide a livestock feedlot operation which utilizes a feed that is efficient in terms of weight gain, that enables the elimination of anabolic steroids and antibiotics, and that reduces livestock flatulence.

Another objective of the present invention is to provide cattle feeding enclosures with concrete slatted floors and manure collection systems so as to prevent contamination of the manure by dirt, water, or other foreign materials that would interfere with the organisms used in the anaerobic digestion system.

Another objective of the present invention is to utilize "High Saturation" wet distillers' grains with solubles ("WDGS") feed rations for beef and/or dairy cattle such that conversion efficiencies and the animals' health are significantly improved, and meat/milk quality is significantly improved.

Another object of the present invention is to reduce/eliminate the incidence of *E. coli* in beef cattle by utilizing "high saturation" WDGS rations to eliminate acidosis, typically caused by excessive starch in the feeding ration.

Another object of the present invention is to ensure the reliable supply of WDGS, in required quality and quantities, to ruminant animals by locating the ethanol unit adjacent to their confinement location, thus eliminating long distance transport and the need for expensive drying.

Another object of the present invention is to reduce/eliminate the use of anabolic steroids and growth hormones, made possible by the increased conversion efficiencies achieved with "high saturation" WDGS rations with their "high bypass" (into the second stomach) characteristics.

Another objective of the present invention is to reduce/eliminate the use of antibiotics in cattle feedlots, by creating a much more sanitary environment through use of concrete slatted floors, immediate manure collection, and anaerobic digestion system.

Another objective of the present invention is to utilize the "natural" concentrated protein in WDGS to improve the starch: protein balance of the traditional cattle ration, and enable the replacement of external protein sources such as urea and alfalfa hay, thus reducing feeding costs, and simplifying a cattle operation's sourcing and inventory requirements.

Another objective of the present invention is to reduce/eliminate cattle feedlot odor and water contamination by rapid transfer of the cattle waste into the anaerobic digestion system, and destruction of the pathogens by the conversion of the cattle waste into bio-gas, bio-fertilizer, and bio-sludge.

Another object of the present invention is to make the production of biofuels like ethanol and bio-gas cost competitive with fossil fuels, by exploiting synergies to reduce capital and operating costs, and maximizing returns on all of the co-products.

Another object of the present invention is to eliminate the need for the capital intensive, and costly to operate and maintain, spent grain mash drying equipment in the ethanol plant.

Another object of the present invention is to substantially reduce the emissions of greenhouse gases such as $CO_2$ and methane to the atmosphere, thus reducing the threat of global warming.

Another object of the present invention is to eliminate the economic costs, and fossil fuel consumption and emissions, that arise from the conventional practice of transportation between disaggregated production sites (e.g., corn fields, corn drying facilities, ethanol plants, and cattle feedlots).

Another objective of the present invention is to reduce the use of fossil fuel fertilizers, and break the nitrogen/phosphate build-up cycle that is causing massive "dead zones" in the Gulf of Mexico and other waterways due to field runoff.

The present invention positively addresses the foregoing objectives, and departs from conventional practice by continuous integration of three sub-systems:

1) a feedyard which encloses livestock over slatted floors for manure disposal and contamination prevention, disease control, and climate protection;
2) an anaerobic digestion/bio-fertilizer recovery system, which collects manure from below the slatted floors and converts it into bio-methane and bio-fertilizer; and
3) an ethanol plant, without traditional spent grain mash drying equipment, and which is powered by the bio-gas recovery energy system.

Taken together, the three "sub-systems" of the present invention, which have never before been integrated in a continuous operation, create the conditions for cost-effective production of "clean beef", ethanol, and bio-gas, and simultaneous reductions in environmental pollution linked to livestock feeding operations. Each of the three "subsystems" is dependent upon the other, from the perspective of both operational and economic efficiencies. For example, the ethanol plant would require expensive mash drying equipment if there were no feedlot; the anaerobic digestion system would not be economically viable if the ethanol plant could not utilize its bio-methane; and the slatted floor feedlot design is critical to prevent manure contamination from interfering with the efficient operation of the anaerobic digestion system.

The present invention differs from conventional practice in several important ways:

1) Ethanol production and livestock feeding are done at the same site, and the animals fed in covered, slatted concrete floor lots. The concrete floors prevent manure contamination by dirt, water, and other foreign materials, and are essential for the cost effective conversion of cattle waste into bio-gas by the anaerobic digestion unit. This manner of animal husbandry also prevents prolonged animal exposure to disease-bearing wastes, and costly weight losses associated with mud and cold exposure, even in northern climes.

Integration of an ethanol unit with the feedlot justifies the investment in an anaerobic digestion unit, since the ethanol plant (unlike the feedlot standing alone) can utilize the bio-gas produced from the livestock waste. At current electricity and natural gas prices, the fossil fuel energy savings—from the combination of elimination of mash drying and the use of the bio-gas —amounts to millions of dollars annually.

2) The sizes of the ethanol unit and the feedlot can be balanced so that all of the high protein WDGS can be fed "wet" directly to the cattle, without capital- and energy-intensive drying, and freight. Compared to a conventional ethanol plant of the same capacity, the present invention's simplified ethanol plant's capital costs will be reduced by up to 30%. In effect, the present invention's ethanol unit serves dual purposes as the feed pretreatment center for "clean beef" and as a plant for producing ethanol as a "co-product".

3) A feeding ration of 25% or more WDGS ("high saturation" WDGS) feeding reduces/eliminates acidosis and liver failure, which have been linked to the formation of *E. Coli* 0157:H7 ("*E. Coli*") in ruminant animals such as beef cattle.

4) Operations and maintenance requirements are greatly simplified, and overall labor costs are reduced. The most important simplifying factor is the elimination of equipment and process duplication in grain handling, energy systems, infrastructure, transportation, etc. However, other operating benefits come from the enclosure of the cattle, the easy proximity of the WDGS for ration formulation, and the improved management of the manure.

5) $CO_2$ may be captured from the ethanol unit, and used for meat processing or other applications. All process water is recycled for use in the digester, ethanol plant, or for irrigation of nearby fields, other parts of the operation. In short, waste is virtually eliminated, and emissions of both $CO_2$ and methane are substantially reduced.

DESCRIPTION OF THE PREFERRED EMBODIMENTS

Figure 1:
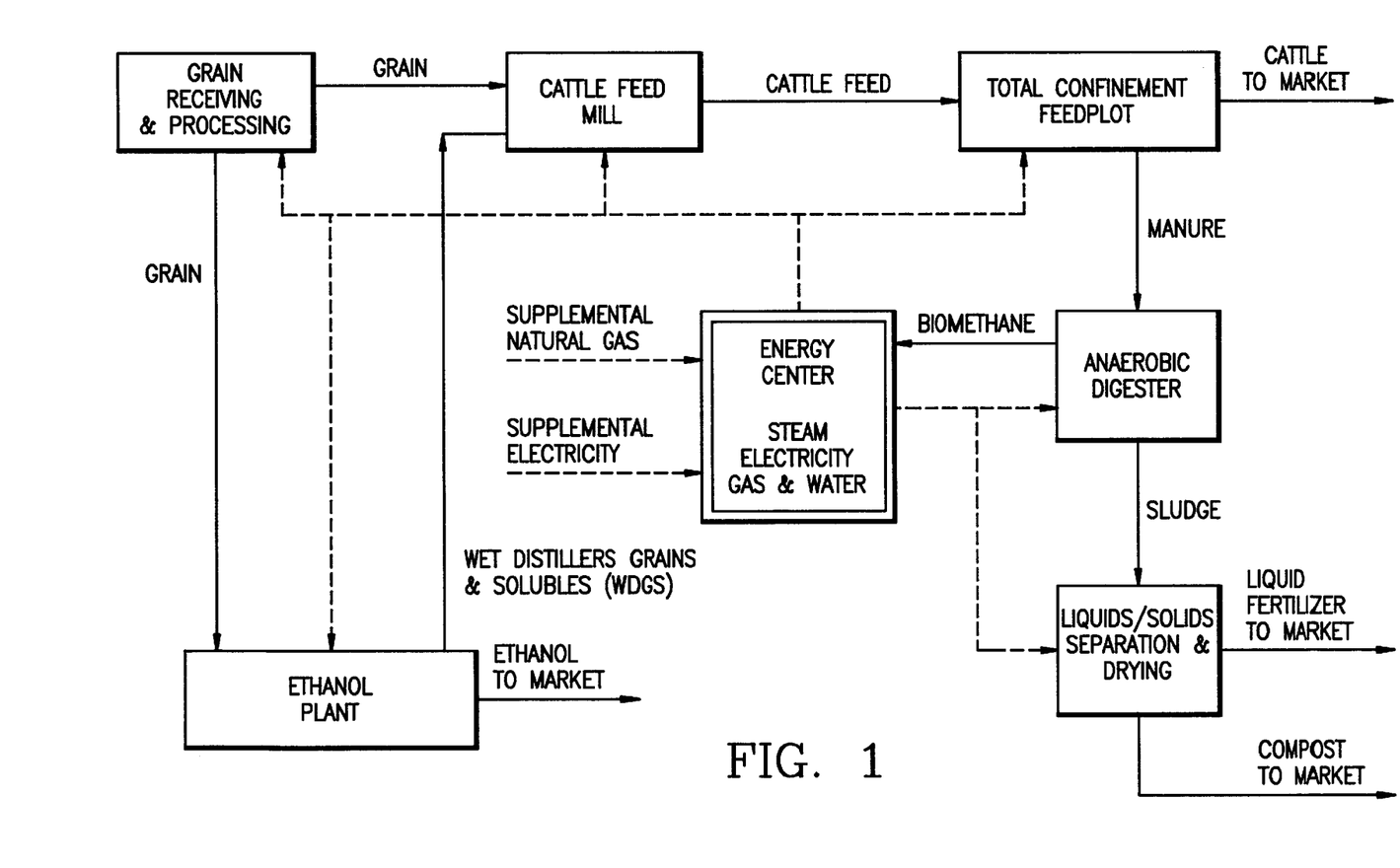
FIG. 1 is a block diagram of a preferred embodiment of the present invention in which the three primary subsystems, along with the common energy complex, are integrated in a continuous operation for the production of "clean beef" or milk, ethanol, wet distillers' grains with solubles, and bio-gas/bio-fertilizer/bio-solids.

FIG. 1 depicts the process with illustration of the major apparatus components utilized therein. Corn from a source bin is fed to a conventional milling device, preferably like those used in "dry mill" ethanol plants 12, for preparing the feed to the ethanol fermenters 16. The major products of the fermentation are carbon dioxide 14, ethanol 18 and WDGS 20. The WDGS 20 is fed to a feed mixer 22 wherein it is blended with a ratio of WDGS:grain of 25:75 to 80:20. The mixed feed 24 is then passed to a cattle feedlot 26 where cattle or other livestock are fattened prior to processing. The beef from the cattle feedlot is slaughtered and routed to an on-site meat packing plant 30 to produce a "clean beef" product 32. Manure 28 is collected from the cattle feedlot and fed to digesters 34 to produce a bio-gas (principally methane) 38 and a clean fertilizer 36. The bio-gas is routed to an energy conversion device 40 which produces non-fossil energy for running the integrated complex. Preferably, the energy conversion device is a combustor with turbines driven by the hot combustion gas to generate electricity in the conventional manner. The manure digestor 34 is either a mechanical continuous-flow digestor or a plug-flow digestor.

Ethanol Synthesis

The ethanol synthesis unit 20 may employ a variety of fermentation organisms, ranging from conventional yeast strains used in most modern ethanol plants, to advanced fermentation organisms such as *Zymomonas mobilis,* the benefits of which are described in U.S. Pat. No. 4,731,329 issued to Lawford, and U.S. Pat. No. 5,070,016 issued to Hallberg. In a preferred embodiment, where the ethanol unit is capable of processing not only the seed portion of the corn, but also cellulosic feedstocks such as the cornstalks—thereby lowering raw material costs—the use of *Zymomonas mobilis*—type organisms would be practiced.

In most cases, however, the operation of the ethanol synthesis unit employed in the present invention will be identical to those in operation today, with the important exception of the spent grain (protein byproduct) drying equipment. The present invention makes possible the elimination of this equipment, resulting in approximately 30% less capital cost, and substantial reductions in plant energy, labor and operations and maintenance costs.

Integration of cattle feedlots and ethanol units provides powerful synergy. Both the feedlot and ethanol operations utilize corn as their principal feedstock and the existing rural infrastructure is suited for both (i.e. grain storage, handling, is treating and transporting). An adjacent ethanol production facility produces a product that is of critical importance to a "clean" cattle ration-dried distillers grains and solubles (DDGS) or wet distillers grains and solubles (WDGS). The distinguishing factor between the two is of course the significant difference in moisture content of the two products.

Distillers' grain by-products are the residual grain mash remaining after the starch has been extracted, converted to sugar and fermented into ethanol and carbon dioxide. Distillers grains contain all of the fiber, proteins, oil, vitamins and minerals of the original feedstock. Virtually all of today's ethanol plants produce dried DGS because their customers are removed from their plant, and wet DGS cannot be transported long distances.

The two different methods of manufacturing ethanol are "dry milling" and "wet milling". The dry mill method involves bringing whole grains into the process that are ground up and fed into the process to be cooked with water. With the second method, wet milling, whole dry grains are steeped in a mild solution of water and acid to loosen the outer fiber covering the grain which is then separated into the different fractions (starch, germ, oil, fiber, proteins, etc.).

The advantage of the wet milling of corn is in the more diverse by-product options, i.e., starch, corn sweeteners, ethanol, corn oil, high and low protein products, fiber and others. The disadvantage is the initial capital investment required to enter this business. In addition, minimum economies of scale for a new wet-milling facility require a capacity to process 25 million bushels of corn per year, and preferably 50 to 75 million bushels per year. These large facilities require hundreds of millions of dollars in initial capital investment, and produce thousands of tons of protein co-products that must be dried thoroughly before being shipped long distances. (WDGS, with its high moisture content, is expensive to transport long distances, and will spoil unless used within several days, particularly in the summer months.)

In the present invention the dry milling of the grain, e.g., corn fed to the ethanol fermenters is preferred because a dry mill ethanol unit is much less capital and energy intensive than a wet milling unit. Affordable economies of scale allow plants as small as 2 million bushels of corn processing per year. A typical dry mill ethanol plant produces three basic products: ethanol, DDGS (animal feed) and carbon dioxide.

In conventional practice, an efficient dry mill ethanol unit will consume approximately 35,000 BTU's of energy to produce the average gallon of ethanol, spent grain and other products. (Approximately 50% of this energy is used to dry the spent grain to form DDGS).

Consequently, there are many cost and operational benefits to be gained from integrating a dry mill ethanol unit (without mash drying) with a cattle feedlot and an anaerobic manure digestion system.

Integration of a cattle feedlot with a dry mill ethanol plant yields an additional, and unexpected advantage—a significant improvement over the traditional cattle ration in terms of increased conversion efficiencies, lower net cost of gain, and improved quality of beef. Accordingly, an important feature of the present invention is the substitution of 25% or more, preferably 75–80%, of the dry matter (DM) content of the typical feeding ration by wet distillers' grains with solubles (WDGS) from the ethanol unit. In recent tests at the 40% substitution level, it has been shown that this reliance upon "high saturation" WDGS increases feed conversion efficiency by 9%. This improvement in conversion efficiency is believed attributable to the fact that the ethanol cooking and fermentation process "predigests" the fiber in the corn. The WDGS also contains a higher protein to starch ratio than the conventional feed ration because the fiber, corn oil, protein, vitamins, minerals, and brewers' yeast are concentrated by a factor of three during the ethanol manufacturing process. This occurs because the corn contains 70% starch and approximately 30% other ingredients. When fermentation takes place, only the starch portion is utilized and the remainder is recovered as WDGS. When the dry matter and oil is accounted for, it results in a significant concentration of the remaining ingredients. A beef animal will consume and convert these WDGS ingredients more efficiently than corn dry matter.

The balance of the cattle feed ration will be corn, trace minerals, nutrients and extra fiber, if needed.

Cattle are typically fed Number Two Yellow Corn, which contains approximately 9–10% protein on average. When corn is converted to ethanol, the resultant WDGS contains approximately 30% protein, on a dry matter basis. The typical feed ration for beef cattle is approximately 11–13% protein. Corn alone can't provide all of the cattles' protein needs. External sources of protein, such as urea, soybean mean, cotton seed meal and alfalfa hay are needed. These protein sources are typically the most expensive ingredient in the ration. However, in the present invention, "high saturation" WDGS feeding means that the corn provides all of the protein required. The WDGS ration is both a naturally occurring protein (thus results in more efficient conversion), and is less expensive. It also has the advantage of allowing the feeding operation to eliminate its sourcing and inventory burdens by two or more ingredients, especially urea and alfalfa.

When beef animals' diet is altered to include large amounts of WDGS, the standard high starch (relative to protein) ratio is reduced. This starch/protein balance improvement also has a beneficial effect. When cattle are fed heavy starch diets they gain well but also tend to develop liver problems. These liver problems come from the starch converting to sugar within the animals two stomachs (rumens). This elevated sugar level deteriorates the liver causing an increased production of methane gas (flatulence) and the need for additional antibiotics to keep the animal healthy. By reducing the starch intake and replacing it with WDGS, the animal is healthier and gains more body weight per pound of feed while lowering its methane gas release.

A primary reason that the use of "high saturation" WDGS rations is not conventional practice is that WDGS is not reliably available in commercial quantities at acceptable prices and quality. In the present invention, the WDGS will be fed as 30% dry matter and 70% moisture. However, with this high moisture content the feed cannot be transported long distances, and quality controlled, in a cost competitive manner. The WDGS has a short shelf life during periods of high heat and humidity and it is a difficult product to handle and store at the feedyard. Consequently, only by practicing the present invention, and intentionally sizing an ethanol unit that is located next to the feedlot's cattle population, can a reliable supply of requisite volumes and quality WDGS be ensured.

Thus, the present invention utilizes high levels of WDGS feeding. As a corn replacement on a dry matter ("DM") basis, feeding wet distillers grains and solubles (WDGS) at high percentages ("high saturation" WDGS rations, at 25% or higher of corn DM by volume) has a number of advantages over conventional feeding practices:

- it improves livestock conversion efficiencies (thus making it economic to eliminate the use of anabolic steroids);
- it reduces starch content of the diet and improves the health of the animal;
- it reduces the need to treat the feed ration with antibiotics;
- it improves the texture of the meat without increasing, or in many cases even reducing, its fat content;
- it reduces feeding costs per pound of gain; and
- it reduces cattle flatulence (a major source of methane emissions) by as much as 50%.

The Feedlot

Figure 2A:
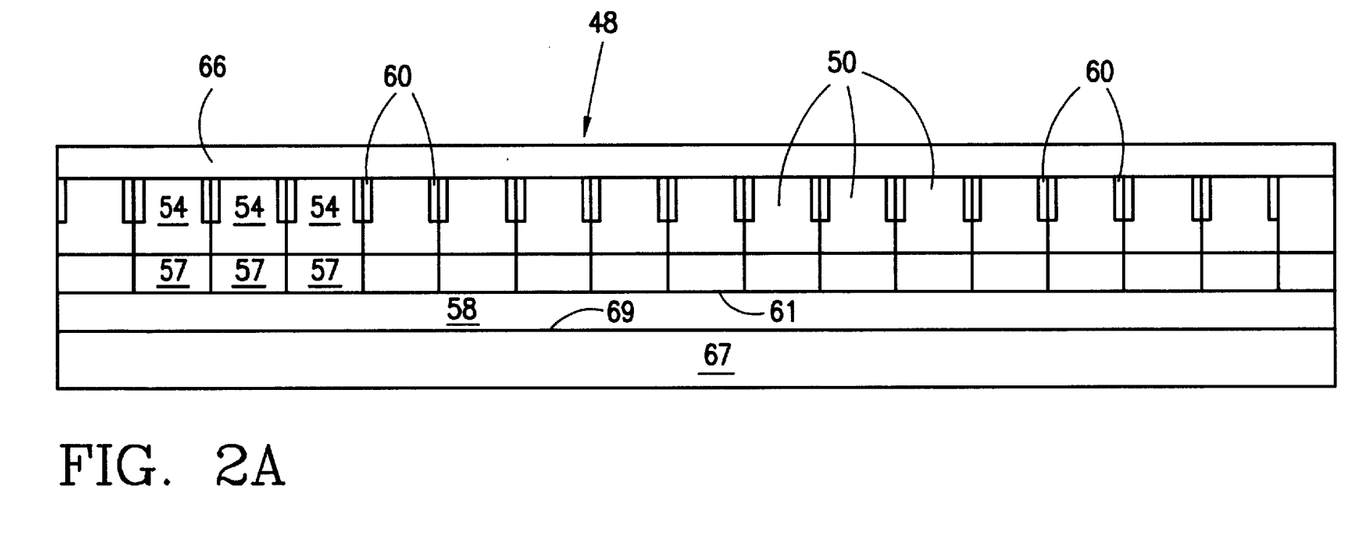
FIGS. 2A and 2B are, respectively, plan and side views of a preferred cattle feeding pen for use in the present invention.
Figure 2B:
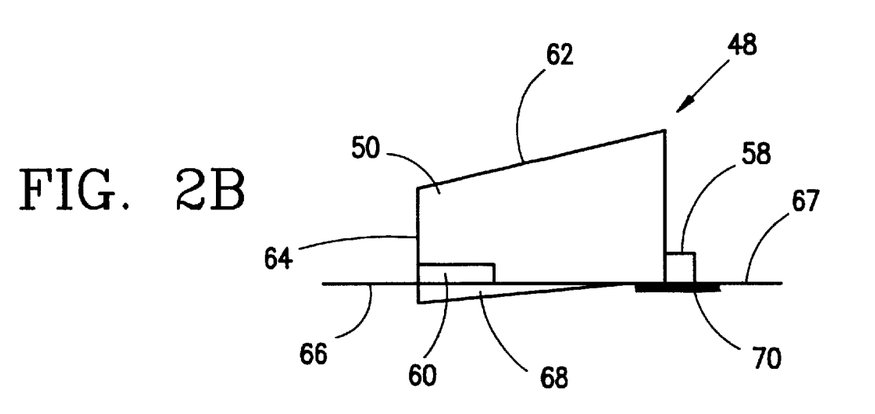
Figure 3:
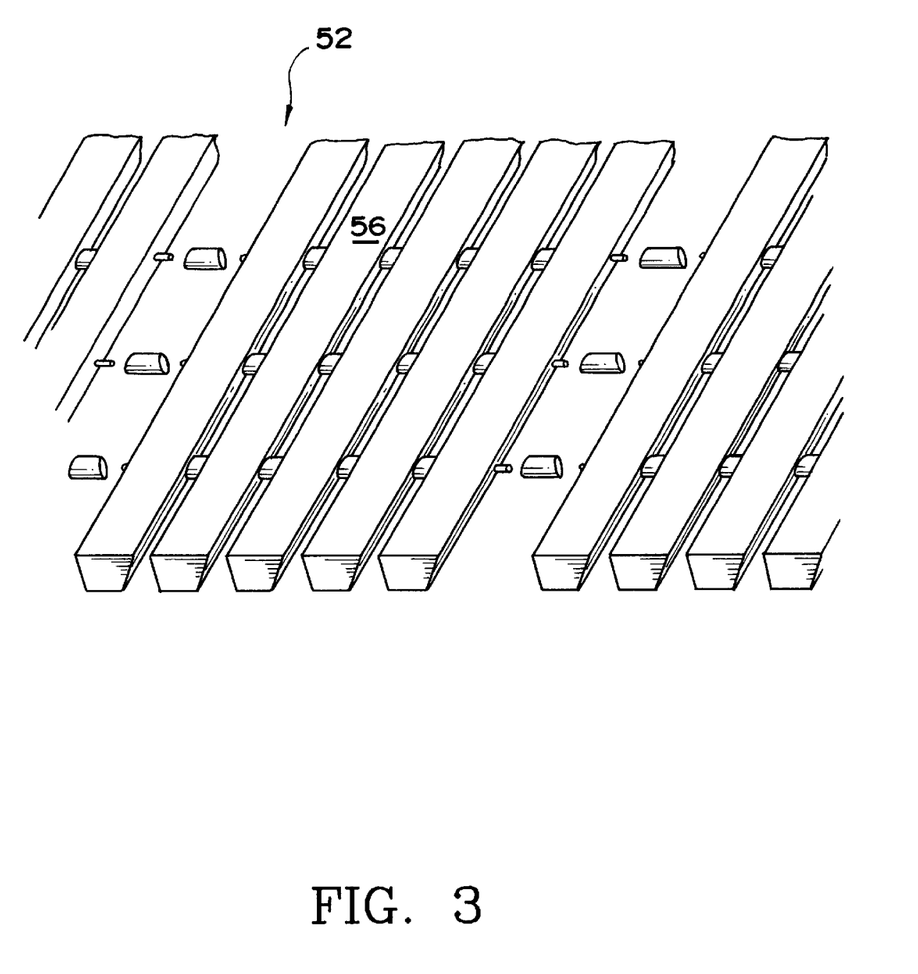
FIG. 3 is a perspective and schematic view of a portion of one floor panel.

FIGS. 2A and 2B illustrate one embodiment of the manure collection, cattle feeding confinement facility, or feedyard. In its preferred embodiment, a shed 48 encloses pens 50 which are constructed so that each animal has approximately 30 square feet of floor space. For descriptive purposes, a feedyard with 50,000 head enclosed capacity would have some of the following characteristics: Each pen 50 would measure 40 feet deep by 150 feet long, with a divider fence (not shown) at 75 feet that makes two pens holding 100 head each. The floor is constructed of slatted concrete panels that are 4 feet wide and 12 feet long. There are three panels 52 laid end to end for a 36×4 foot floor 54. The floor panels 52 are formed of reinforced concrete slats 56, as shown in FIG. 4. Each concrete slat is 4" wide and the spacing between adjacent slots is 1.5".

The pen floor 54 has a four foot solid section 57 at the feed bunks 58 end for extra safety and comfort for the cattle while they are feeding. Between each pen there is a shared water trough 60. Each side of each pen has a water trough. This allows for some maintenance and repair downtime while never allowing the pen to run out of water.

The pens 50 are covered by a roof 62 that is much higher at the front than the rear. This allows for rain and snow coverage and runoff. The front of the shed 48 is facing south. This allows for maximum light all day. The design takes advantage of the summer and the winter solstice. During the winter, the sun shines all the way to the back of the pens 50. During the summer, the pens are shaded. Each shed 48 is 2400 feet long, and is enclosed on the east and west sides. The back or north side has ventilation slats 64 that can be manually adjusted. In addition, two back panels may be added for weather and temperature control in late fall and early winter. During the winter, the pen is protected from the north wind and snow, and provides the animals with a dry, warm environment compared to conventional, open dirt floor confinement facilities.

Beneath the slatted floor 54 is a shallow trough 68, which directs the manure into the initial preparation tanks of the anaerobic digester.

The pens 50 are gated at the back into a paved alleyway 66, which allows the entry and exit of the cattle. The paving is important, as it prevents dirt and foreign materials from getting into the manure, and contaminating the anaerobic digestion system.

Concrete-constructed feed bunks 58 are located on a paved alleyway at the front of the pens and run the entire 2500 feet of the pen row. The feed bunk 58 is four feet wide at the top and 3 feet wide at the bottom, with a front panel 59 higher than rear panel 51 to prevent spillage. Feeding occurs twice daily, or more if needed. Each animal requires 8 to 10 inches of bunk space on average and eats off and on all day. When the cattle are not eating, they lay in the back of the pen while others are feeding. A feed delivery truck brings the special "high saturation" WDGS ration that is prepared fresh daily for each pen. Access for the feed delivery truck is provided by a 12 foot paved feed alley 67. An 8 foot wide concrete mat 70 is provided under the feed bank 58. Concrete mat 70 helps with clean-up and is sloped to prevent surface water from entering subfloor sites.

Anaerobic Digestion

Anaerobic digesters are mechanical devices that utilize biological organisms in the absence of oxygen to convert cattle or other manure into marketable by-products. A properly operated digester will eliminate manure odors, destroy the pathogens and convert the manure to methane gas, liquid fertilizer and compost which can be sources of income for the feedyard. In addition, the environment and neighboring areas are vastly improved.

Traditional cattle feedyards cannot take advantage of anaerobic digesters due to the conventional practice of placing cattle pens on dirt rather than concrete. Scraping the surface layer of manure lying on dirt yields both manure and soil. Microorganisms in soil destroy the active organisms in anaerobic digesters and dirt clogs the digestor space. Ultimately, dirt and sand are extremely harmful ingredients in the pumps and basins and result in digester failure. Surface runoff and rain water also deplete storage lagoons and spoil digester activation and similarly, will also render digesters inoperable.

Anaerobic digestion systems have seen limited use in actual practice. There are two basic types of digesters: plug flow, and mixed mechanical. The plug flow anaerobic digestion process is the most common, primarily because it costs less to build (especially without economies of scale), and is easier to operate. Plug flow systems have seen limited use in dairy operations, and virtually no use in cattle feedlots. The disadvantages of a plug flow anaerobic digestion system are numerous:

- It is extremely sensitive to feed consistency (both composition quality and quantity)
- It does not lend itself to scaleup, and beyond 4,000 head of ruminant animals requires many parallel units and increased complexity of operation.
- Due to impurities, the bio-gas must be treated prior to use in expensive electrical devices such as turbines or fuel cells.
- It requires periodic shut-downs for cleaning and cover replacements.

It is a slow process which requires 3–4 weeks to complete the digester cycle.

For the present invention, mechanical (mixed) digesters have more advantages, and less disadvantages. Advantages include:

They can handle multiple feedstocks at one time.

They are less sensitive, and they are less susceptible to "upset".

Their feedstock composition quality may vary.

They require smaller space to build and operate.

They are easy to operate.

They produce higher quality products, including bio-gas with less impurities.

Accordingly, the preferred embodiment of the present invention uses a conventional, mechanical continuous digestor. However, both plug flow and mechanical mixed digesters are acceptable.

Mechanical digestion systems do require more initial capital investment, and more training for operations and maintenance. Due to their higher capital cost, they are more sensitive to economies of scale (larger is better).

In the present invention, anaerobic digestion of the manure from a 25,000 head commercial cattle feedyard would produce enough bio-gas to make approximately two megawatts of electricity. One important reason that conventional feedlots do not have anaerobic digesters is that there is no outlet for this volume of bio-gas, so that investment in the electrical turbines and exhaust heat recovery systems cannot be economically justified. However, with the present invention, the integration of the ethanol unit creates sufficient demand for both bio-gas-generated electricity, and the exhaust heat (low-pressure, low-BTU steam) from the turbines to justify the investment in the anaerobic digester.

The digester will produce a liquid fertilizer that can be applied to farm fields to supplement or eliminate commercial fertilizers needed for crop production. Current research indicates that liquid fertilizer from an anaerobic digester is more readily available in the soil than commercial chemical fertilizers. And, this treated waste stream can be easily applied though irrigation equipment or sprayed on the fields with traditional equipment. Unlike solid or liquid fresh manure, this solution does not have to be incorporated into the soil within 12 hours of spreading because the pathogens and dangerous compounds found in animal manure are destroyed in the digestion process.

In terms of odor control, the digester deals with the objectionable manure odors by converting the manure into clean-burning bio-gas or pathogen-free liquid fertilizer and compost. Because cattle digest only 70% of their feed, many organic compounds remain undigested in the manure. The active organisms in an anaerobic digester convert these organics into acids, which are then attacked by other organisms in the digester and converted into methane and other gases. In the process, the pathogens and compounds that cause odor are destroyed.

Another advantage of the anaerobically-digested manure liquid by-product is that it can be applied to growing plants/crops, not just empty fields, which will extend the application time from approximately three months out of the year to six months out of the year. After treatment in an anaerobic digester, the nitrogen in the bio-fertilizer is in a more stable form. It does not have to be incorporated deep into the ground in order to prevent losing its nitrogen to the atmosphere. It can also be stored in inexpensive lined ponds through periods of winter when the ground is frozen. Unlike the raw, untreated manure, this liquid fertilizer is not harmful to the environment.

The solids that remain from an anaerobic digester make for good quality compost material. This is the organic matter than was not digested by the cattle or converted into acids and ultimately methane gas. The solids can be separated by rotating and shaking screens. Centrifuges should be avoided due to their higher capital and operating costs. The compost can be sold as a value-added by-product to retail garden shops, landscape developers or simply re-applied on the farm field as a soil supplement. If the product is used on farm fields it will raise the productivity of the soil and should produce more crops per acre.

The anaerobic digestion sub-system as employed in the present invention has not seen widespread commercial usage due to the absence of synergies. However, the present invention economically justifies investment in a anaerobic digestion system, which:

prevents feedlot manure contamination of the air, land and water supplies;

reduces cattle-related methane releases to the atmosphere;

reduces insect infestations and thus diseases;

destroys pathogens and largely eliminates odors;

generates sufficient bio-gas to displace most of the fossil fuel required in the entire complex;

produces an odor-free bio-fertilizer that can be put back onto the fields without environmental damage (can replace significant amounts of fossil fuel-based fertilizers);

produces a high-grade pathogen-free organic compost that can be marketed to the gardening industry or field applied;

ensures that the animals thrive in a relatively clean, weather-controlled environment, which is of critical importance to the production of "clean beef".

Preferably, the complex would have access to sufficient farmland which could also serve as the bio-fertilizer and bio-sludge application area. In the preferred embodiment, the liquids portion or bio-fertilizer would be pumped through a center point irrigation system to adjacent fields and applied to growing plants, thus greatly increasing the acceptable period for application. This method would also significantly increase the value of the bio-fertilizer. The solids portion of the digester process can also be applied to the fields for soil enhancement purposes, or sold as organic compost to golf courses or other users.

Methane Utilization

In addition to its protection against water contamination and odor pollution, the most significant attribute of the anaerobic digester is its ability to greatly reduce, if not eliminate, the environmental release of methane gas from cattle feedlots. Animal manure rapidly degrades into methane gas. Worldwide, cattle are the largest non-industrial source of methane emissions into the atmosphere.

As the anaerobic digester converts digestible organics in the manure to methane, the gas is extracted and scrubbed for use as a fuel. With the present invention, the methane recovered from the anaerobic digestion operation can be utilized in the complex to generate needed steam or to replace fossil fuel-generated electricity purchased from local utilities. Any excess can be sold back to the electrical grid, and would be eligible for "green or renewable power tax credits" which makes this electricity more valuable than fossil fuel produced power. Under newly proposed federal legislation, in the near future greenhouse gas credits (GHGC's) may have a monetary value which is currently estimated to be approximately $10 to $20 per ton of carbon equivalent (methane is 22 times as potent a GHG than carbon dioxide).

If the methane is first used to power electricity-producing devices, the exhaust heat can also be recovered and used to heat water for steam purposes. Steam too, can be successfully utilized by the feedyard for its source of flaking corn. In the preferred embodiment, by using a mechanical continuous flow anaerobic digester for manure management, relatively "clean" medium-BTU bio-gas (700–800 BTU's per cubic foot) is produced. During the mechanical process, hydrogen sulfide and other harmful sulfur components are recovered. This bio-gas is then separated into methane and other gases, and used in on-site for generation of electricity and "waste" steam. The low-pressure steam is perfect for use in the ethanol unit, and feedmill.

Greenhouse Gas (GHG) Reduction

Compared to conventional practice, the present invention will substantially reduce GHG emissions of $CO_2$ and methane.

Carbon Dioxide

Carbon dioxide emissions are reduced through the following:

1) The primary raw material of the present invention is corn or other feed grain. During photosynthesis, an acre of corn extracts more $CO_2$ than two acres of mature Amazon rain forest. Only the seed of the corn plant is used, with the rest returned to the earth where it acts as a "carbon sink". As noted below, surface application of the bio-fertilizer from the complex also allows the use of low input ridge till farming, as opposed to the more energy intensive "deep plowing" practices. This significantly reduces fossil fuel usage, and further augments the "carbon sink" effect, which helps to prevent soil erosion.

2) Due to the elimination of mash and protein byproduct drying, and the use of bio-methane instead of natural gas or other fossil fuels, ethanol is produced with a highly positive energy balance. Renewable ethanol, when substituted for petroleum-based fuels, reduces imported oil use on a 2:1 basis (two gallons of crude oil displaced for each gallon of ethanol used as an octane enhancer).

3) Utilizing the same bushel of corn to produce both meat and fuel results in extremely high conversion efficiencies, and substantially reduces petroleum consumption per bushel of corn produced (field preparation, cultivation, harvesting, fertilizers, chemicals, and transport).

4) Bio-fertilizer recapture and pathogen extermination (odor removal) allows energy efficient surface application back to the fields, and reduces petroleum and natural gas requirements for fertilizer manufacture, transport, and application.

5) Complexes utilizing the present invention are able to utilize high moisture (24% per bushel moisture content) corn picked directly from the field. This eliminates the energy normally consumed in corn drying (typically 14–15% moisture levels), and the petroleum consumed in transportation to and from the fields and the drying points.

6) Processing of both food and fuel at the same location will reduce overall transportation-related petroleum requirements, and costs, by 25% or more.

7) Feeding WDGS avoids not only the energy costs of drying, but also replaces petroleum-based urea in the feed ration.

8) In the preferred embodiment of the present invention, the capture and use of the $CO_2$ from the ethanol unit for meat processing and other purposes prevents its venting to the atmosphere, and saves fossil fuel-generated electricity used in both refrigeration and chemical processing for meat sterilization and transportation.

Methane (22 Times More Potent Than $CO_2$ as a GHG)

Methane emissions are reduced through the following mechanisms:

1) By changing feed rations from predominantly dry corn to corn and WDGS, cattle flatulence is reduced by as much as 50%. By immediately capturing the manure through the slatted floors, most of the methane emissions to the atmosphere from the manure are also eliminated. Livestock-related methane releases account for a substantial portion of U.S. methane emissions.

2) The bio-gas recovered from the manure will be used to replace natural gas and other fossil fuels used for both electrical and steam generation (bio-fuels displace essentially 100% of the fossil fuel requirements of the entire complex). In large operations, excess energy can be sold to the grid.

3) The bio-fertilizer from the ZPF2 Complex is pathogen-free, which allows surface application back to the fields (even while crop growth is occurring), and the use of low input ridge till farming instead of deep plowing. This further reduces petroleum requirements.

Meat Packing

As discussed above, using the present invention, properly designed feedlots—integrated with an ethanol unit for ration improvement and an anaerobic digestion unit for sanitary control—can finish out "clean beef" that will be antibiotic-, growth hormone- and *E.coli*-free. Using high-saturation WDGS rations, the cattle will gain weight more efficiently, will not suffer from acidosis linked to *E. coli,* and despite lower fat content, will have exceptional taste and tenderness characteristics. Cattle raised in such a manner should command higher price premiums. However, if the cattle were processed in conventional packing plants, much, or all, of this premium could be lost.

Consequently, a preferred embodiment of the present invention is the co-location of a dedicated "clean beef" packing plant adjacent to the complex itself, as depicted in FIG. 2.

In current practice, conventional feedlots supply packing plants with cattle that have been fed rations with high volumes of antibiotics, anabolic steroids and growth hormones, and high starch to protein ratios that lead to acidosis (and *E. coli*). In addition, modern packing plants do not completely process the beef for consumer retail purchase; they cut the beef into large sections, known as "boxed beef". This includes loins, ribs, butts, and other large cuts that are normally Cryovac-packed, boxed and handled with forklifts. The box cuts are shipped to wholesale warehouses, bulk-break plants and large local supermarkets. Local meat butchers break down the box cuts into retail case goods.

Many of these local operations cut steaks, roasts and ribs and send the trimmings to other locations for further processing into ground beef and hamburger. Each of these steps increases the opportunity for contamination. *E-coli* and other intestinal pathogens are sometimes allowed to touch the meat during slaughter. These pathogens can contaminate meat products by transmission from the employees' hands, knives, and equipment, and by coming in contact with the floor. If these contaminants are only on the outer fat of the meat products, it is normally cut away before processing into final cuts for retail sale. However, if this contamination is ground into the hamburger it is then spread to the entire batch in process. If the plant and its employees do not take adequate precautions and sterilize the equipment on a regular basis, it can be passed to future batches as well.

Two of the major cost centers of a meat packing plant are electricity costs for refrigeration and freezing, and the treatment of wastes, both paunch manure and waste-water. Both of these cost centers can be integrated into the operations of the overall feedlot/ethanol/anaerobic digestion complex, and net costs greatly reduced. Excess electricity generated by the bio-gas turbines can be used in the dedicated "clean beef" packing plant rather than sold to the grid. Further, the ethanol unit's $CO_2$ can be easily captured and sent "across the fence" for refrigeration, sterilization, and freezing applications. Finally, the continuous flow anaerobic digestion system can be interconnected, and adapted to treat packing plant wastes for a modest incremental investment.

In summary, the present invention substantially reduces fossil fuel use, livestock methane emissions and other pollution, and transform wastes into valuable products. As a result, substantial reductions in GHGs are achieved cost effectively, and efficiently. The net effect of these reductions should be of great benefit to the agricultural sector in the future as mechanisms are established for trading greenhouse gas emission reduction credits.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. An integrated continuous process for the production of ethanol and a bio-gas containing methane comprising:

(a) fermenting grain in an aqueous medium to produce ethanol in said medium, a wet distillers' grain with solubles as a wet grain residue, and carbon dioxide;

(b) feeding the wet grain residue to livestock in a feedlot having slatted floors, said wet grain residue constituting 25–80% of a feed ration of said livestock on a dry weight basis, said feed ration consisting essentially of said 25–80% wet grain residue and grain;

(c) collecting manure produced by the livestock from beneath the slatted floor;

(d) digesting the collected manure anaerobically with microorganisms to produce the bio-gas containing methane and, as a residue, a bio-fertilizer;

(e) combusting said bio-gas to produce heat; and (f) dry milling the grain used in step (a) for fermenting to produce ethanol utilizing the heat produced by said combusting.

2. A process according to claim 1 wherein said digesting is either plug flow or mechanical continuous flow digesting.

* * * * *

UNITED STATES PATENT AND TRADEMARK OFFICE
CERTIFICATE OF CORRECTION

PATENT NO. : 6,355,456 B1
DATED : March 12, 2002
INVENTOR(S) : Hallberg et al.

It is certified that error appears in the above-identified patent and that said Letters Patent is hereby corrected as shown below:

<u>Title page,</u>
Item [56], References Cited, OTHER PUBLICATONS, insert -- Evaluation of Wet Distillers Grains for finishing Cattle, A.S. Leaflet R1342 --.

Signed and Sealed this

Eighteenth Day of May, 2004

JON W. DUDAS
*Acting Director of the United States Patent and Trademark Office*